US006937883B2

(12) United States Patent
Prince

(10) Patent No.: US 6,937,883 B2
(45) Date of Patent: Aug. 30, 2005

(54) SYSTEM AND METHOD FOR GENERATING GATING SIGNALS FOR A MAGNETIC RESONANCE IMAGING SYSTEM

(76) Inventor: Martin R. Prince, 1161 York Ave., Apt. 10H, New York, NY (US) 10021

( * ) Notice: Subject to any disclaimer, the term of this patent is extended or adjusted under 35 U.S.C. 154(b) by 93 days.

(21) Appl. No.: 10/440,844

(22) Filed: May 19, 2003

(65) Prior Publication Data

US 2003/0195413 A1 Oct. 16, 2003

(Under 37 CFR 1.47)

Related U.S. Application Data

(63) Continuation of application No. 09/520,916, filed on Mar. 8, 2000, now abandoned.

(51) Int. Cl.[7] ............................................... A61B 5/055
(52) U.S. Cl. ..................... 600/411; 600/413; 600/437; 600/443; 600/453; 600/534
(58) Field of Search ...................... 600/411, 413, 600/437, 443, 449, 453, 508, 534

(56) References Cited

U.S. PATENT DOCUMENTS 5,032,793 A * 7/1991 Yamamoto et al. ......... 324/309
6,198,959 B1 * 3/2001 Wang ......................... 600/413

* cited by examiner

*Primary Examiner*—Ruth S. Smith
(74) *Attorney, Agent, or Firm*—Neil A. Steinberg

(57) ABSTRACT

A magnetic resonance imaging system is disclosed to perform an imaging pulse sequence that acquires data to generate an image of at least a portion of the patient. The magnetic resonance imaging system comprises an acoustic transducer to irradiate an anatomic structure in the patient using ultrasonic energy. A receiver, in response to ultrasonic energy, generates echo signals. Using the echo signals, a signal analyzer generates a plurality of gating signals, including a first gating signal in response to a first period of motion of the anatomic structure and the second gating signal in response to a second period of motion of the structure. The magnetic resonance imaging system, in response to the first gating signal, acquires data from the center of k-space, and, in response to the second gating signal, acquires the periphery of k-space.

22 Claims, 4 Drawing Sheets

SYSTEM AND METHOD FOR GENERATING GATING SIGNALS FOR A MAGNETIC RESONANCE IMAGING SYSTEM

This application is a continuation of Application Ser. No. 09/520,916, filed Mar. 3, 2000, now abandoned.

BACKGROUND OF THE INVENTION

The field of the invention is nuclear magnetic resonance imaging methods and systems. More particularly, the invention relates to the accurate generation of cardiac gating signals for use in MR imaging and spectroscopy.

The data required to reconstruct an MR image is acquired by an MRI system over a period of time. In most acquisitions this time period extends over many cardiac cycles of the patient and sometimes it is necessary to synchronize the acquisition with the cardiac cycle. This is accomplished in most applications by monitoring an ECG signal produced by the patient's heart and triggering, or gating, the data acquisition sequence when the R-peak in the QRS complex is detected.

The accurate detection of the R wave peak in the ECG signal is very difficult in an MRI system environment. First, the quality of the ECG signal itself is seriously degraded by the magnetic induction effects caused by the strong magnetic fields used in MRI systems. Significant inductive noise is added to the ECG signal by patient movement, heart motion, and blood flow as well as "gradient noise" produced by the rapidly changing magnetic field gradients used during MRI acquisitions. Under the best conditions the production of a reliable ECG trigger signal is very challenging.

In a large number of patients the ECG gating does not work well. In patients who are large with a lot of subcutaneous fat, who have chronic obstructive pulmonary disease with expanded lungs, or for other reasons, the ECG signal may be small and difficult to detect within the electrically noisy environment of an MR imaging system. In addition, the magnetic field influences the shape of the ECG signal. This change in the shape of the ECG signal may make it difficult to correctly synchronize off the QRS complex. This is because the T wave may be increased in size and become difficult to distinguish from the QRS complex.

A solution to this problem has been to use a pulse oximeter such as that disclosed in U.S. Pat. No. 5,743,263 to gate from detected flow related changes in the finger tip. However, the detection of systole at the finger tip is delayed compared to systole in the ventricles. The timing between the two will depend on multiple factors including vascular tree compliance, vascular tree resistance, cardiac output, distance from the heart to name only a few. As a result, this often is not useful for "freezing" the motion of the heart.

In addition to cardiac imaging, there are other situations in which cardiac gating is required. For flow imaging in peripheral vessels, frequently one wants to image these vessels when they contain the maximum amount of flow, i.e. during systole. In this situation ECG is problematic because of the time delay problem discussed above. That is, the timing of systole at a peripheral vessel may be very different than systole at the heart.

Another modality for producing images uses ultrasound. There are a number of modes in which ultrasound can be used to produce images of objects. In the so-called "A-scan" method, an ultrasound pulse is directed into the object by an acoustic transducer and the amplitude of the reflected sound is recorded over a period of time. The amplitude of the echo signal is proportional to the strength of scatterers in the object and the time delay is proportional to the range of the scatterers from the transducer. In the so-called "B-scan" method, the transducer transmits a series of ultrasonic pulses as it is scanned across the object along a single axis of motion. The resulting echo signals are recorded as with the A-scan method and their amplitude is used to modulate the brightness of pixels on a display at the time delay. With the B-scan method, enough data are acquired from which a 2D image of the scatterers can be reconstructed. Another way to represent ultrasound information is called "M-mode". In this technique, a single B-mode line is reproduced repeatedly and displayed as a time plot with the ordinate corresponding to position along the line and the abscissa representing time. If there is motion along the line, the pixel brightnesses are modulated as structures move in and out of or along the line of sight. Thus moving objects are well represented in this mode.

Ultrasonic transducers for medical applications are constructed from one or more piezoelectric elements sandwiched between a pair of electrodes. Such piezoelectric elements are typically constructed of lead zirconate titanate (PZT), polyvinylidene diflouride (PVDF), or PZT ceramic/polymer composite. The electrodes are connected to a voltage source, and when a voltage is applied, the piezoelectric elements change in size at a frequency corresponding to that of the applied voltage. When a voltage waveform is applied, the piezoelectric element emits an ultrasonic wave into the media to which it is coupled at the frequencies contained in the excitation waveform. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is coupled to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231.

When used for ultrasound imaging, the transducer often has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave that travels along a preferred beam direction and is focused at a selected point along the beam. By controlling the time delay and amplitude of the applied voltages, the beam with its focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the signal from each transducer array element.

This form of ultrasonic imaging is referred to as "phased array sector scanning". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction ($\theta$) during each measurement to acquire data from a series of points along an acoustic beam or scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio.

Cardiac gating is also used when performing ultrasonic imaging. As disclosed in U.S. Pat. No. 5,709,210, for example, when cardiac gating is required a standard ECG signal is used to trigger the image acquisition.

SUMMARY OF THE INVENTION

The present invention is a detector system for producing a plurality of gating signals, including a first gating signal and a second gating signal, for an MRI system. More particularly, the detector system includes an ultrasonic transducer positioned to insonify an anatomic structure of a patient, a receiver connected to the ultrasonic transducer for receiving echo signals which are indicative of the movement of the anatomic structure and a signal analyzer for producing the plurality of gating signals for the MRI system when a preselected characteristic in the echo signals is detected. The magnetic resonance imaging system, in response to the first gating signal, acquires data from the center of k-space of the imaging sequence and in response to the second gating signal acquires data from the periphery of k-space of the imaging sequence. The ultrasonic transducer may be placed, for example, on the patien's chest to detect specific cardiac movements or blood flow, or it may be located to detect the motion of specific peripheral blood vessels or the blood flow in the vessels.

The invention provides a reliable gating signals for an MRI system. The ultrasonic transducer produces a signal which is less susceptible to interference and distortion from the magnetic fields produce in a MRI system environment. Its amplitude is much greater than an ECG signal and it is based on physical motion of the subject rather than electrical signal.

The invention also provides a plurality of accurate and predictable gating signals, including a first gating signal, in response to a first period of motion of the anatomic structure, and a second gating signal in response to a second period of motion of the anatomic structure. The ultrasonic transducer may be positioned to detect movement of many different structures. The structure which provides the optimal timing for the image being acquire can thus be used as the basis for the gating signals. Such a structure may be, for example, a particular blood vessel or a particular heart structure such as a chamber wall or heart valve. Specific blood flow in the heart such as the atrial kick can be detected as a marker for end-diastole. Further, respiratory gating can be accomplished by detecting the motion of the diaphragm.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
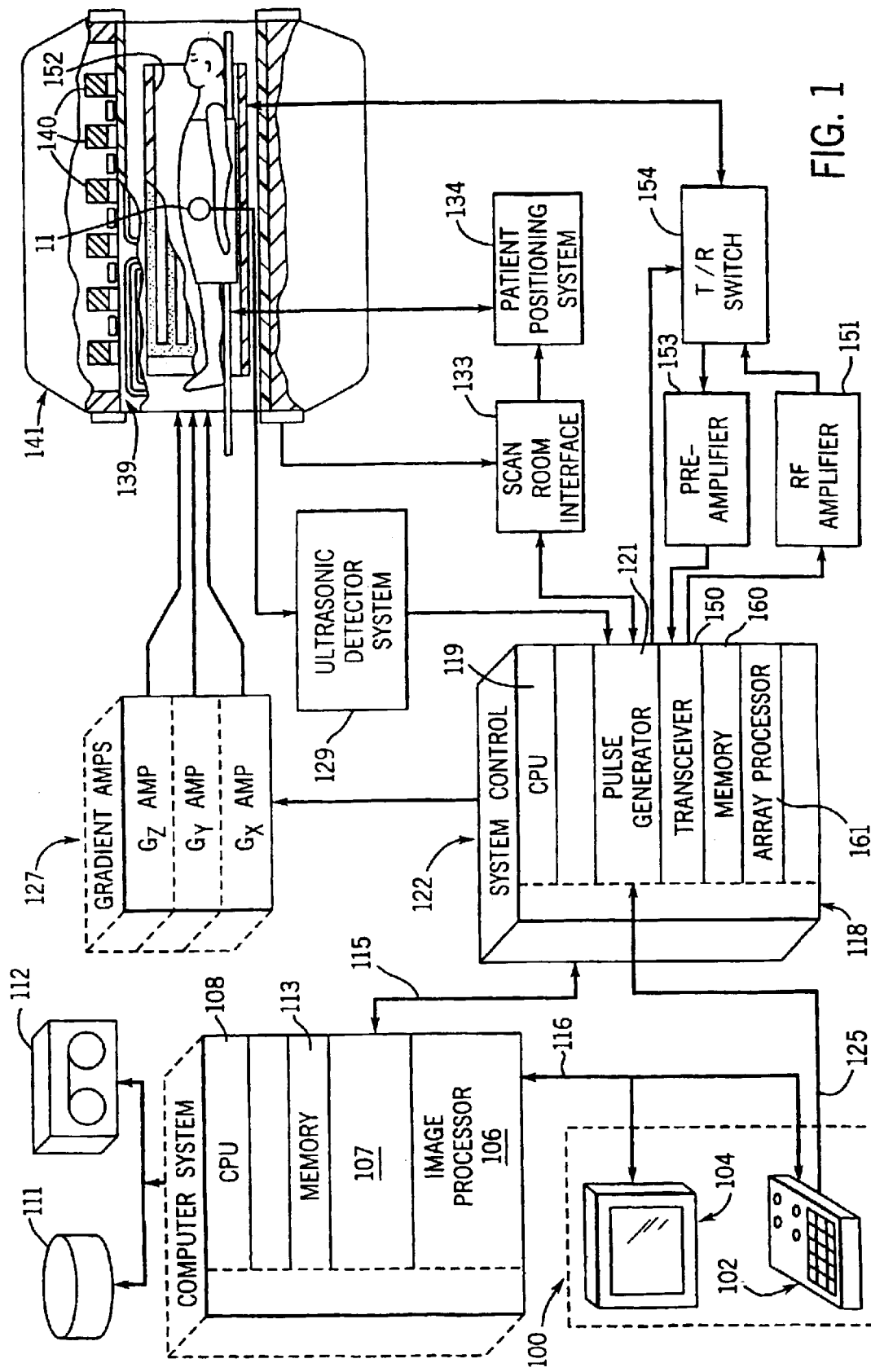
FIG. 1 is a block diagram of an MRI system which employs the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan.

The system control 122 receives a gating signal from an ultrasonic detector system 129. As will be described in more detail below, the detector system 129 receives an electrical signal from an ultrasonic transducer 11 that is positioned to sense motion in the patient. This electrical signal is analyzed to produce a gating signal for the pulse generator module 121. This gating signal serves to trigger the acquisition of NMR data using the pulse sequence prescribed by the operator.

The pulse generator module 121 also connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, it is conveyed through a backplane 118 to an array processor 161 which operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104.

As will become apparent from the description below, the ultrasonic detector system 129 can take many forms. In the preferred embodiment a system capable of producing sector scanning gray scale images is used. The ultrasonic transducer 11 is located in the bore of the magnet 141 and is positioned on the patient and acoustically coupled to the anatomy of interest. The transducer is connected with a cable to the ultrasonic detector system 129 which is located outside the scan room. Electrical shielding is employed to prevent the strong electromagnetic fields produced by the MRI system from interfering with the signals produced by the ultrasonic transducer 11.

Before the patient is placed in the bore of the magnet 141 the ultrasonic transducer 11 is properly positioned to detect the movement of a chosen anatomic structure. This is accomplished by acquiring ultrasonic images and moving the transducer until the chosen anatomic structure is properly displayed in the image. The ultrasonic detector system also includes a Doppler processor and the operator places the range gate for this Doppler processor over the chosen anatomic structure. The frequency of sound waves reflecting from the identified anatomic structure is shifted in proportion to the velocity of the structure; positively shifted for movement toward the transducer and negatively shifted for movement away from the transducer. As will be explained in more detail below, the Doppler processor computes these frequency shifts. These Doppler signals are used to produce the gating signal for the MRI, and when a reliable gating signal is obtained, the patient is moved into the bore of the magnet 141 and the scan is performed.

Figure 2:
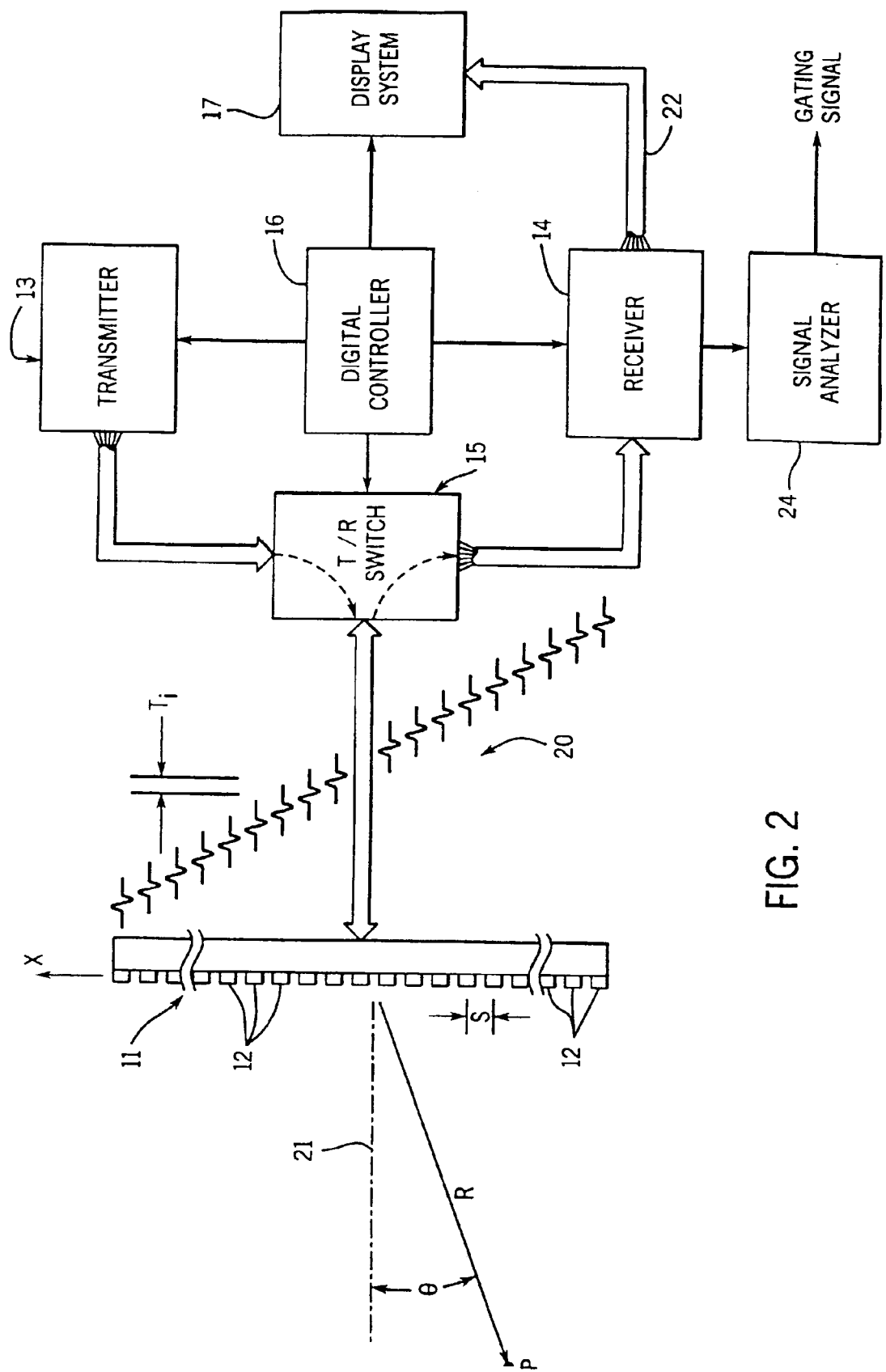
FIG. 2 is a block diagram of an ultrasound detector system employed in the MRI system of FIG. 1 to produce an ECG signal.

Referring particularly to FIG. 2, the ultrasonic imaging detector system 129 includes a transducer array 11 comprised of a plurality of separately driven elements 12 which each produce a burst of ultrasonic energy when energized by a pulsed waveform produced by a transmitter 13. The ultrasonic energy reflected back to the transducer array 11 from the subject under study is converted to an electrical signal by each transducer element 12 and applied separately to a receiver 14 through a set of transmit/receive (T/R) switches 15. The transmitter 13, receiver 14 and the switches 15 are operated under the control of a digital controller 16 responsive to the commands input by the human operator. A complete scan is performed by acquiring a series of echoes in which the switches 15 are set to their transmit position, the transmitter 13 is gated on momentarily to energize each transducer element 12, the switches 15 are then set to their receive position, and the subsequent echo signals produced by each transducer element 12 are applied to the receiver 14. The separate echo signals from each transducer element 12 are combined in the receiver 14 to produce a single echo signal which is employed to produce a line in an image on a display system 17.

The transmitter 13 drives the transducer array 11 such that the ultrasonic energy produced is directed, or steered, in a beam. A B-scan can therefore be performed by moving this beam through a set of angles from point-to-point rather than physically moving the transducer array 11. To accomplish this the transmitter 13 imparts a time delay ($T_i$) to the respective pulsed waveforms 20 that are applied to successive transducer elements 12. If the time delay is zero ($T_i$=0), all the transducer elements 12 are energized simultaneously and the resulting ultrasonic beam is directed along an axis 21 normal to the transducer face and originating from the center of the transducer array 11. As the time delay ($T_i$) is increased as illustrated in FIG. 2, the ultrasonic beam is directed downward from the central axis 21 by an angle θ.

The time delays $T_i$ have the effect of steering the beam in the desired angle θ, and causing it to be focused at a fixed range $R_T$. A sector scan is performed by progressively changing the time delays $T_i$ in successive excitations. The angle θ is thus changed in increments to steer the transmitted beam in a succession of directions. When the direction of the beam is above the central axis 21, the timing of the pulses 20 is reversed.

Referring still to FIG. 2, the echo signals produced by each burst of ultrasonic energy emanate from reflecting objects located at successive positions (R) along the ultrasonic beam. These are sensed separately by each segment 12 of the transducer array 11 and a sample of the magnitude of the echo signal at a particular point in time represents the amount of reflection occurring at a specific range (R). Due to the differences in the propagation paths between a focal point P and each transducer element 12, however, these echo signals will not occur simultaneously and their amplitudes will not be equal. The function of the receiver 14 is to amplify and demodulate these separate echo signals, impart the proper time delay to each and sum them together to provide a single echo signal which accurately indicates the total ultrasonic energy reflected from point P located at range R along the ultrasonic beam oriented at the angle θ.

To simultaneously sum the electrical signals produced by the echoes from each transducer element 12, time delays and phase shifts are introduced into each separate transducer element channel of the receiver 14. The beam time delays for reception are the same delays ($T_i$) as the transmission delays described above, However, in order to dynamically focus, the time delay and phase shift of each receiver channel is continuously changing during reception of the echo to provide dynamic focusing of the received beam at the range R from which the echo signal emanates.

Under the direction of the digital controller 16, the receiver 14 provides delays during the scan such that the steering of the receiver 14 tracks with the direction of the beam steered by the transmitter 13 and it samples the echo signals at a succession of ranges and provides the proper delays and phase shifts to dynamically focus at points P along the beam. Thus, each emission of an ultrasonic pulse waveform results in the acquisition of a series of data points which represent the amount of reflected sound from a corresponding series of points P located along the ultrasonic beam.

The display system 17 receives the series of data points produced by the receiver 14 through bus 22 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles ($\theta$) is performed to provide the data necessary for display.

A signal analyzer 24 connects to the receiver 14 and analyzes the echo signal to detect movement of the reflectors along the beam. As will be described in more detail below, the signal analyzer produces a gating signal for the MRI system each time a specific movement is detected.

Figure 3:
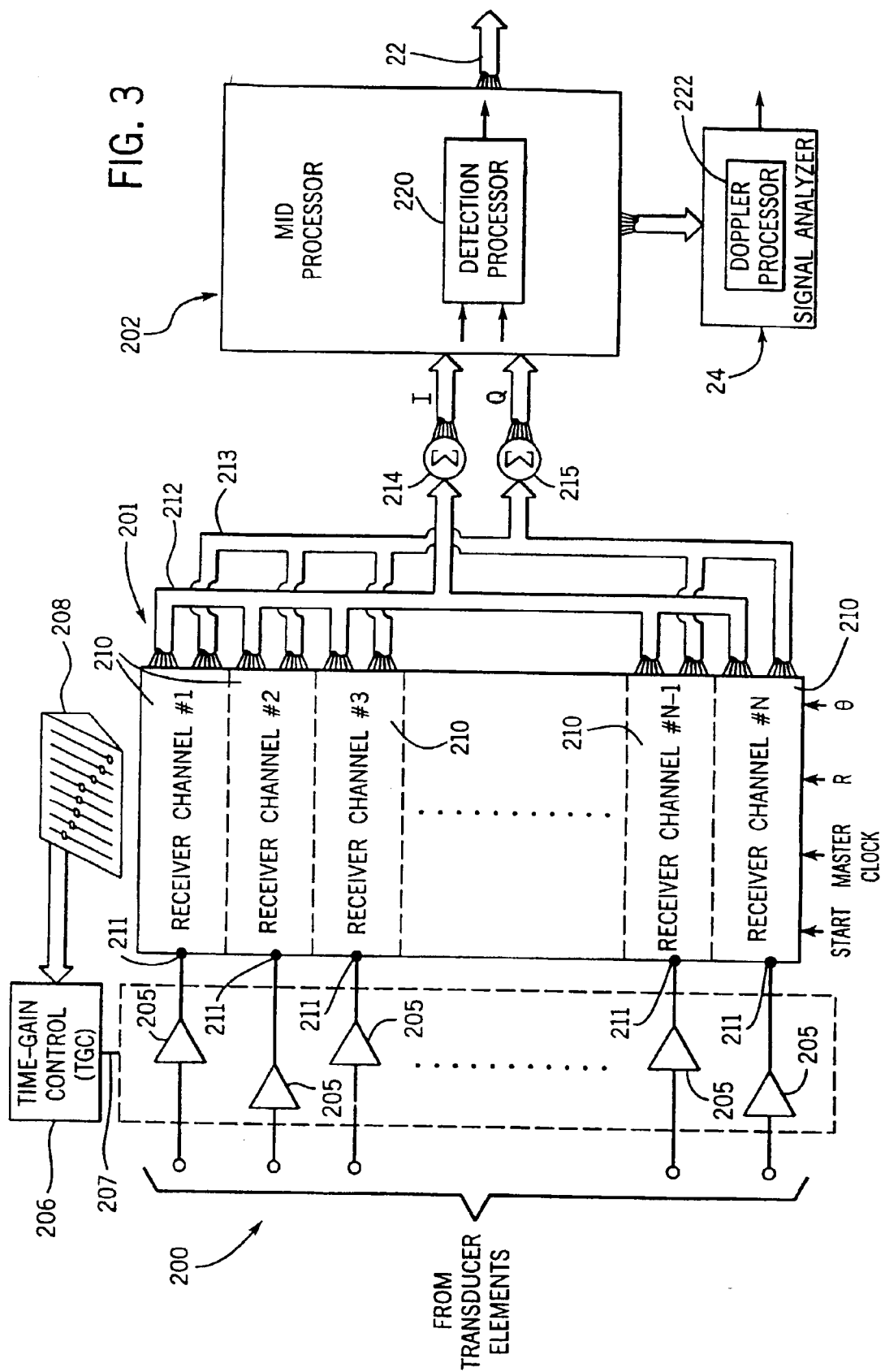
FIG. 3 is a block diagram of a receiver which forms part of the ultrasound detector system of FIG. 2.

Referring particularly to FIG. 3, the receiver 14 is comprised of three sections: a time gain control section 100, a beam forming section 201, and a mid processor 202. The time-gain control section 200 includes an amplifier 205 for each of the N=64 receiver channels and a time-gain control circuit 206. The input of each amplifier 205 is connected to a respective one of the transducer elements 12 to receive and amplify the echo signal which it receives. The amount of amplification provided by the amplifiers 205 is controlled through a control line 207 that is driven by the time-gain control circuit 206. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets eight (typically) TGC linear potentiometers 208 to values which provide a relatively uniform brightness over the entire range of the sector scan. The time interval over which the echo signal is acquired determines the range from which it emanates, and this time interval is divided into eight segments by the TGC control circuit 206. The settings of the eight potentiometers are employed to set the gain of the amplifiers 205 during each of the eight respective time intervals so that the echo signal is amplified in ever increasing amounts over the acquisition time interval.

The beam forming section 201 of the receiver 14 includes N=64 separate receiver channels 210. Each receiver channel 210 receives the analog echo signal from one of the TGC amplifiers 205 at an input 211, and it produces a stream of digitized output values on an I bus 212 and a Q bus 213. Each of these I and Q values represents a sample of the echo signal envelope at a specific range (R). These samples have been delayed and phase shifted such that when they are summed at summing points 214 and 215 with the I and Q samples from each of the other receiver channels 210, they indicate the magnitude and phase of the echo signal reflected from a point P located at range R on the steered beam ($\theta$).

Referring still to FIG. 3, the mid processor section 202 receives the beam samples from the summing points 214 and 215. The I and Q values of each beam sample is a digital number which represents the in-phase and quadrature components of the magnitude of the reflected sound from a point (R, $\theta$). When the ultrasonic detector system 129 is in an imaging mode, a detection process indicated at 120 is implemented in which a digital magnitude M is calculated from each beam sample and output at 22 to the display system, where $M=\sqrt{I^2+Q^2}$.

As described in U.S. Pat. No. 5,349,525 which is incorporated herein by reference, these magnitude values M are accumulated during the scan and converted to display data that produces a two-dimensional, sector scan image of the anatomic structures irradiated by the ultrasonic transducer 11.

When switched to a Doppler mode of operation, the ultrasonic detection system 129 transmits and receives echo signals from a single beam angle ($\theta$). Referring still to FIG. 3, in this mode of operation the mid processor 202 couples the I and Q beam samples to the signal analyzer 24. The signal analyzer 24 includes a Doppler processor 222 such as that described in U.S. Pat. No. 4,217,909 issued on Aug. 19, 1980 and entitled "*Directional Detection of Blood Velocities In An Ultrasound System*"; or such as that described in U.S. Pat. No. 4,265,126 issued on May 5, 1981 and entitled "*Measurement of True Blood Velocity By an Ultrasound System*". Such Doppler processors employ the phase information ($\phi$) contained in each beam sample to determine the velocity of reflecting objects along the direction of the beam (i.e. radial direction from the center of the transducer 11), where $\phi=\tan^{-1}(I/Q)$.

The Doppler processor 222 stores a succession of 2 msec. segments of beam sample data and performs a fast Fourier transformation on each segment. The result is a spectra signal which indicates the frequency components of the echo signal.

The signal analyzer 24 processes the Doppler spectra signal to produce a logic level gating signal for the MRI system. A number of methods may be used depending on the anatomic structure selected to produce the gating signal. In one embodiment a high pass filter is used to remove all but the high frequency components. The level of the frequency components above the selected frequency are monitored, and if any high frequency components are detected, rapid motion of the selected anatomic structure is indicated and a gating signal is produced. In another embodiment, the mean value of the frequency spectrum from the Doppler processor 222 is calculated, and a gating signal is produced when this mean value exceeds a preset frequency. In another embodiment, the gating signal may be produced when the mean value changes rapidly, i.e. the derivative exceeds a preset value. Such an implementation is useful in gating from blood turbulence. The gating signal is a TTL logic level signal identical to that produced by ECG gating systems.

Figure 5:
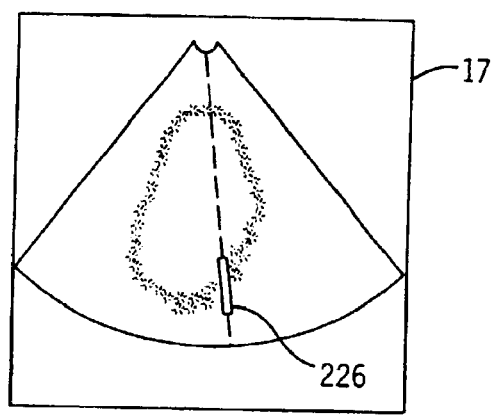
FIG. 5 is a pictorial representation of an ultrasonic image used to select a heart wall as the detected anatomic structure.

When operated in the Doppler mode, the ultrasonic detector system 129 periodically updates the display with a 2D sector scan image of the irradiated anatomy. Such an image is shown in FIG. 5 where the selected anatomy is the heart. When gating from the heart the transducer 11 is positioned on the patient to acquire echo signals from either a peristernal short axis view or an apical long axis view. Gating signals can be produced using heart wall motion, mitral valve motion or blood flow. The beam angle from which a gating signal is to be acquired is set by the operator using a control panel associated with the digital controller 16. The operator positions a "range-gate" on the 2D image as indicated at 226 to select the area of interest. The anatomic structure indicated by this range gate will serve as the moving structure used for gating. Such range gate positioning is described, for example, in U.S. Pat. No. 5,785,655, which is incorporated herein by reference. It is the echo signal data from the area selected by the range gate that is applied to the Doppler processor 222 and used to produce the gating signal.

Figure 6:
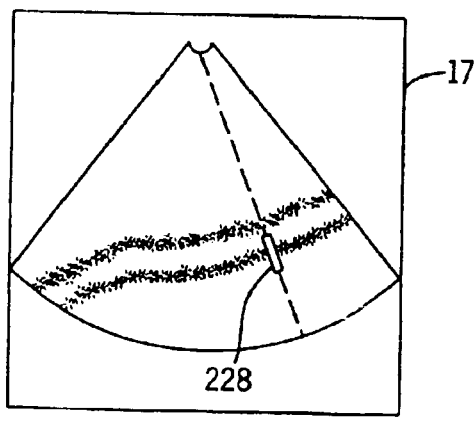
FIG. 6 is a pictorial representation of an ultrasonic image used to select a peripheral vessel as the detected anatomic structure.

When used to produce a cardiac gating signal from a peripheral vessel, the ultrasonic transducer 11 is positioned on the patient to acquire a 2D image of the target blood vessel as shown in FIG. 6. A range gate is positioned in the vessel or on the vessel wall as shown at 228. The range gate can either be positioned across the wall of the vessel to detect motion of the vessel wall, or it can be positioned within the vessel to detect pulsatile motion from blood flow. The systolic portion of the heart cycle will generate relatively high frequency shifts compared to the rest of the heart cycle, and these can be detected by the methods described above to provide a gating signal. This strategy will work for any vessel in which a sample volume can be positioned.

It should be apparent that the present invention is not limited to cardiac gating. In another embodiment, one may gate off the motion of a muscle, tendon, or another tissue to synchronize with imaging of a moving body part. For example, to gate the image with respiration, one can detect motion of the liver, spleen, or diaphragm. To gate a kinematic study of opening and closing the mouth, one can detect motion of the masseter muscle.

It should be apparent to those skilled in the art that many variations are possible from the preferred embodiment without departing from the spirit of the invention. The ultrasound imaging capability described above is very useful as a means for "aiming" the single beam used to acquire an echo signal from selected anatomic structures for producing a gating signal. However, other means may be employed to accurately irradiate selected anatomic structures. For example, ultrasonic transducers that produce a fixed beam may be located with fixtures or positioned with guiding apparatus that reliably direct the beam at specific anatomic structures. A flat transducer may be placed directly over the carotid artery, for example, to detect wall motion or blood flow toward and away from the transducer. Another location of interest is the point of maximum cardiac impact (PMI) on the patient's chest.

In these embodiments the transducer is placed on the patient and adjusted until a reliable gating signal is produced. No ultrasonic image is acquired. Such an implementation would be particularly appropriate for continuous wave (CW) Dopplers in which no image is generated. CW Dopplers would most likely be restricted to blood flow detection, or simple displacements such as motion of the patient's diaphragm.

Figure 4:
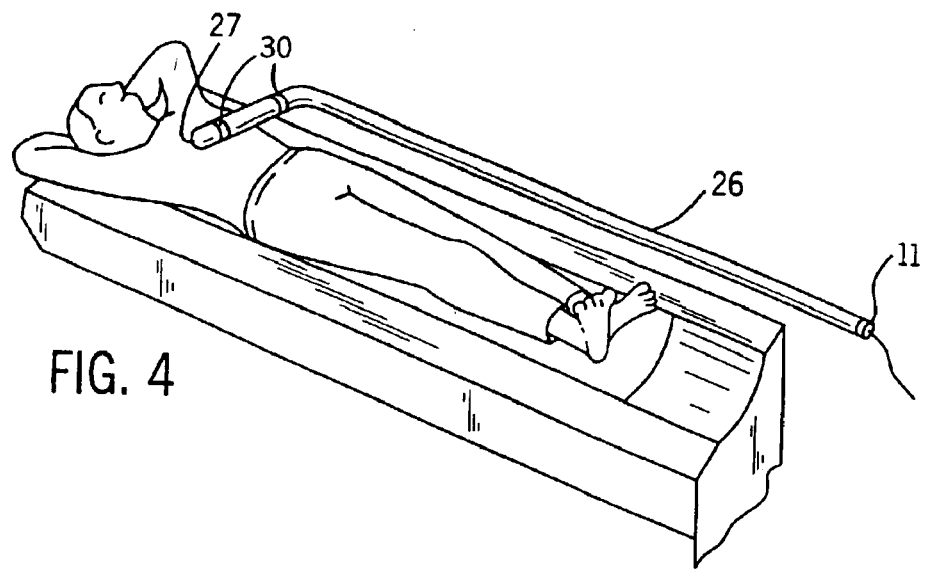
FIG. 4 is a pictorial representation of an alternative way to couple an acoustic transducer to a patient.

In some situations it is desirable to remove the ultrasonic transducer 11 and its associated conductors and shielding away from the bore of the magnet 141 and well outside the field of view of the MRI system. Referring to FIG. 4, in this case the transducer 11 is remotely located and an acoustic waveguide 26 is used to convey the ultrasonic transmit and receive beams. The waveguide 26 is made of a non-conductive material and it extends into the bore of magnet 141. The ultrasonic transducer 11 is mounted in the proximal end of the waveguide 26 and the distal end 27 bears against the patient's skin and acoustically couples therewith. A lens (not shown) is formed in the distal end 27 of the waveguide 26 to focus the ultrasonic energy at an adjustable distance therefrom.

The waveguide 26 is formed by an outer tube filled with a material that propagates sonic waves efficiently. Many materials can be used, but they should be MR inactive and preferably the tube material should propagate sound at a higher velocity than the filler in order to totally reflect sound. The waveguide 26 should also optimally prevent mode conversion in the walls of the tube. A material such as tygon tubing may be used for the tube and degassed, distilled water may be used for the filler.

Since the beam of sonic energy cannot be scanned or steered when using the waveguide 26 no standard B-mode ultrasonic image can be produced. However, an M-mode image can be generated, and it can be used to position and orient the distal end of the waveguide 27. As those skilled in the art know, M-mode scanning was the standard method for heart ultrasound imaging. As discussed above, when using certain anatomical structures to produce the gating signal, fixtures or guides that engage or attach to the patient may also be used to properly place and orient the distal end 27. A more general method, however, is to use the imaging capability of the MRI system to assist in "aiming" the waveguide 26.

Disposed around the waveguide 26 near its distal end 27 are two bands 30 of MR active material. These bands 30 produce a strong NMR signal and they appear very bright on reconstructed MR images. During setup, a fluoroscopic NMR scan is conducted as described in U.S. Pat. No. 4,830,012 to produce real time images of the target anatomical structure and the distal end 27 of the waveguide 26 The bright guide marks produced in these images by the bands 30 show the location and orientation of the waveguide 26 with respect to the target structure. The operator can adjust the position of the waveguide distal end 27 until the guide marks indicate that an echo signal will be acquired from the desired anatomic structure.

For peripheral vascular imaging, a 1D color Doppler M-mode image may be produced using the waveguide 26. The color Doppler image may be used to identify vessels and used to aim the waveguide 26.

While the present invention has particular application where ECG monitors have traditionally been used, it may also be used in many other applications. For example, the invention may be used to gate off the flow of blood through a selected structure. If the left ventricular outflow tract is selected, for example, one can use the present invention to estimate cardiac output by measuring the mean blood flow velocity through the tract using the ultrasonic detector and multiplying by the cross-sectional area of the tract. The cross-sectional area of the tract can be measured in a scout scan using the MRI system and the ultrasound detector produces the real-time mean velocity signal during the imaging scan. The resulting blood volume flow measurement may be analyzed to produce one or more gating signals for the MRI system, and it may be visually indicated to attending physicians.

The present invention may also be used as a respiratory monitor to produce gating signals indicative of patient respiration. This may be done, for example, by locating the Doppler range gate across the diaphragm by aiming the ultrasound beam through the liver in a longitudinal orientation. When the diaphragm moves, a very high amplitude signal is produced at the output of the Doppler processor because the diaphragm-lung boundary produces a very large reflection. This can be used to follow respiratory rate and rhythm.

The present invention is not limited to the generation of a single gating signal during each functional cycle (e.g. cardiac cycle). Prior art ECG monitors gate off the R-peak in the QRS complex, which occurs once per cardiac cycle. All MRI data is acquired based on this single trigger. The ultrasound detection system of the present invention can provide much more information about the movement, or functioning of the subject anatomy and analysis of the echo signal may produce more than one gating signal. For example, a first gating signal may be produced during a first period of anatomic motion and a second gating signal may be produced during a second period of anatomic motion. The first gating signal may be used by the pulse generator to acquire NMR data from the center k-space and the second gating signal may be used to trigger acquisition of views from the periphery of k-space.

The gating signal produced by the present invention may be more than a simple trigger signal that initiates data acquisition. For example, the gating signal may enable data acquisition for as long as it is present, and when the gating signal turns off, data acquisition is stopped. When applied to cardiac imaging, for example, the gating signal is produced while the heart wall movement within the Doppler range gate is within a preset limit. No assumptions are made about a data acquisition window based on a rhythmic heart rate, the desired acquisition window is actually detected during each heart beat.

What is claimed is:

1. A magnetic resonance imaging system having a magnet, which produces a polarizing magnetic field in which a patient to be imaged is placed, and a pulse generator, which directs the magnetic resonance imaging system to perform an imaging pulse sequence that acquires data wherein the magnetic resonance imaging system uses the data to generate a magnetic resonance image of at least a portion of the patient, the magnetic resonance imaging system comprising:
    an acoustic transducer, capable of being acoustically coupled to irradiate an anatomic structure in the patient using ultrasonic energy;
    a receiver to measure ultrasonic energy reflected by the anatomic structure and to generate echo signals in response thereto;
    a signal analyzer, coupled to the receiver, to generate a plurality of gating signals using the echo signals, including:
        a first gating signal in response to a first period of motion of the anatomic structure, and
        a second gating signal in response to a second period of motion of the anatomic structure; and
    wherein the magnetic resonance Imaging system, in response to the first gating signal, acquires data from the center of k-space of the imaging sequence and in response to the second gating signal acquires data from the periphery of k-space of the imaging sequence.

2. The magnetic resonance imaging system of claim 1 further including an operator monitor, coupled to the receiver, to visually display the echo signals as an image of the anatomic structure.

3. The magnetic resonance imaging system of claim 1 wherein one of the plurality of gating signals initiates data acquisition of the imaging sequence by the magnetic resonance imaging system.

4. The magnetic resonance imaging system of claim 1 further including:
    a monitor, coupled to the receiver, to visually display an image of the anatomic structure; and
    a control panel, including an operator input, to permit a range gate to be positioned on the image of the anatomic structure wherein the range gate indicates an area of interest of the anatomic structure.

5. The magnetic resonance imaging system of claim 1 wherein the signal analyzer includes a Doppler processor to determine a velocity of the first motion of the anatomic structure.

6. A magnetic resonance imaging system comprising:
    a pulse generator to direct the magnetic resonance imaging system to perform an imaging pulse sequence to acquire magnetic resonance image data including data which is representative of the center of k-space and data which is representative of the periphery of k-space;
    an image processor to generate a magnetic resonance image of at least a portion of the patient using the magnetic resonance image data;
    an acoustic transducer to irradiate an anatomic structure in the patient using ultrasonic energy;
    a receiver to measure ultrasonic energy reflected by the anatomic structure and to generate echo signals in response thereto;
    a signal analyzer, coupled to the receiver, to produce a plurality of gating signals using the echo signals, including:
        a first gating signal in response to a first motion of the anatomic structure, and
        a second gating signal in response to a second motion of the anatomic structure; and
    wherein the magnetic resonance imaging system, in response to the first gating signal, acquires the data which is representative of the center of k-space, and in response to the second gating signal acquires data which is representative of the periphery of k-space.

7. The magnetic resonance imaging system of claim 6 wherein one of the plurality of gating signals initiates data acquisition of the imaging sequence by the magnetic resonance imaging system.

8. The magnetic resonance imaging system of claim 6 further including:
    a display system, coupled to the receiver, to convert the echo signals to ultrasonic image data and visually display an image of the anatomic structure; and
    an operator input to permit a range gate to be positioned on the image of the anatomic structure wherein the range gate indicates an area of interest of the anatomic structure.

9. The magnetic resonance imaging system of claim 6 wherein the signal analyzer includes a Doppler processor to determine a velocity of the first motion of the anatomic structure.

10. The magnetic resonance imaging system of claim 6 wherein the signal analyzer includes a Doppler processor to determine a velocity of the first and second motions of the anatomic structure.

11. A method of imaging a patient using magnetic resonance imaging, the method comprising:
    irradiating an anatomic structure in the patient with acoustic energy;
    measuring echo signals wherein the echo signals are reflections of acoustic energy from the anatomic structure;
    analyzing the echo signals to detect motion of the anatomic structure;

generating a plurality of gating signals in response to detecting the motion of the anatomic structure, including:

a first gating signal in response to a first predetermined motion of the anatomic structure, and a second gating signal in response to a second predetermined motion of the anatomic structure;

collecting first image data of a magnetic resonance imaging sequence in response to the first gating signal wherein the first image data is data which is representative of the center of k-space; and collecting second image data of the magnetic resonance imaging sequence in response to the second gating signal wherein the second image data is data which is representative of the periphery of k-space.

12. The method of claim 11 wherein the first image data is collected only while the first gating signal is present and the second image data is image data is collected only while the second gating signal is present.

13. The method of claim 11 further including displaying an ultrasonic image of the anatomic structure using the echo signals.

14. The method of claim 11 further including:

converting the echo signals into ultrasonic image data; and visually displaying an image of the anatomic structure using the ultrasonic image data.

15. The method of claim 14 further including:

indicating an area of interest of the anatomic structure by positioning a range gate on the image of the anatomic structure.

16. The method of claim 11 further including:

generating the plurality of gating signals in response to detecting the motion of the heart of the patient.

17. The method of claim 11 further including:

generating the plurality of gating signals in response to detecting the motion of the diaphragm of the patient.

18. The method of claim 11 further including:

generating a magnetic resonance image using the first image data and the second image data.

19. The method of claim 11 wherein one of the plurality of gating signals initiates collection of image data of an imaging sequence and wherein the imaging sequence includes collecting the first and second image data.

20. The method of claim 11 wherein generating a plurality of gating signals in response to detecting the motion of the anatomic structure includes generating a plurality of gating signals in response to detecting the motion of the diaphragm of the patient.

21. The method of claim 11 wherein generating a plurality of gating signals in response to detecting the motion of the anatomic structure includes generating a plurality of gating signals in response to detecting the motion of the heart of the patient.

22. The method of claim 11 the first image data is collected only while the first gating signal is present.

* * * * *